United States Patent
Kadota et al.

(10) Patent No.: US 7,311,919 B2
(45) Date of Patent: Dec. 25, 2007

(54) AGENTS FOR TREATING OSTEOPOROSIS AND INHIBITING OSTEOCLAST FORMATION

(75) Inventors: Shigetoshi Kadota, Toyama (JP); Yoshinobu Hashimoto, Fujisawa (JP); Chia-Chin Sheu, Kuei Shan Hsiang (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 0 days.

(21) Appl. No.: 11/533,665

(22) Filed: Sep. 20, 2006

(65) Prior Publication Data

US 2007/0014811 A1    Jan. 18, 2007

Related U.S. Application Data

(63) Continuation of application No. 10/825,585, filed on Apr. 16, 2004.

(30) Foreign Application Priority Data

Apr. 17, 2003   (JP)   ............... 2003-112655

(51) Int. Cl.
*A61K 36/068* (2006.01)
*A61P 19/10* (2006.01)
*A61P 3/14* (2006.01)

(52) U.S. Cl. .................. 424/195.15

(58) Field of Classification Search .......... None
See application file for complete search history.

(56) References Cited

U.S. PATENT DOCUMENTS 5,948,404 A *   9/1999   Taketomo et al.
6,558,943 B1 *   5/2003   Li et al.

FOREIGN PATENT DOCUMENTS

| CN | 1051471 C | * | 4/2000 |
| CN | 1356115 A |   | 7/2002 |
| EP | 0 496520 A1 |   | 7/1992 |
| JP | 59078641 A |   | 5/1984 |
| JP | 4-352795 |   | 12/1992 |
| JP | 7-215878 |   | 8/1995 |
| JP | 8-12580 |   | 1/1996 |
| JP | 11-60489 |   | 3/1999 |

OTHER PUBLICATIONS

Li, S. P. et al. Phytomedicince (May 2002), 9(4): 319-24. The fruiting body and its caterpillar host of *Cordyceps sinensis* show close resemblance in main constituents and anti-oxidation activity.*
Zhu, J. S. et al. The Journal of Alternative and Complementary Medicine (1998), 4(4): 429-457. The scientific rediscovery of a precious ancient Chinese herbal regimen: *Cordyceps sinensis*. Part II.*
Koh, Jong-Ho et al. Biosci. Biotechnol. Biochem (Feb. 2002), 66(2): 407-11. Activation of macrophages and the intestinal immune system by an orally administered decoction from.

* cited by examiner

*Primary Examiner*—Michele Flood
(74) *Attorney, Agent, or Firm*—Kristina Castellano; Castellano PLLC

(57) ABSTRACT

Compositions and methods for treating osteoporosis, the formation of osteoeclasts, and/or for the suppression of decreasing spongy bone density. Example methods include administering *Cordyceps sinensis* or its processed product.

8 Claims, 2 Drawing Sheets

AGENTS FOR TREATING OSTEOPOROSIS AND INHIBITING OSTEOCLAST FORMATION

CLAIM FOR PRIORITY

This application is a continuation of U.S. Application Ser. No. 10/825,585 filed on Apr. 16, 2004, which claims priority to Japanese patent application 2003-112655 filed on Apr. 17, 2003, both of which are incorporated herein by reference.

FIELD OF THE INVENTION

The present invention is related to *Cordyceps Sinensis* (*C. Sinensis*) that can prevent the manifestation of osteoporosis. In particular, the present invention is related to the composition for treating osteoporosis and osteoclast formation comprising *C. Sinensis* mycelium as the effective ingredient.

BACKGROUND OF THE INVENTION

The function of bone is to support body against gravity and to conduct movement. As the largest reservoir of calcium in the body, the bone also maintains the balance of calcium in the body. Because of having movement function and maintaining the balance of calcium in the body, the renewal and resorption of bone and the bone will be made repeatedly. During childhood and the adolescent, bone formation is more important than bone resorption, thus bone grows larger, heavier and denser.

The following briefly states how the bone goes through its life cycle through different stages in bone remodeling.

The bone remodeling is mainly regulated by chondrocyte, osteoblast and osteoclast. The bone remodeling can be divided into three stages. That is, (1) bone renewal and growth due to intrachondral bone formation, (2) the cycle of remodeling bone formation and bone resorption to maintain quality and quantity; and (3) re-growth during bone injury such as fracture.

Each stages described above is regulated by various $Ca^{2+}$-dependent enzymes, cytokines, gene transcription and other cellular regulation mechanisms to regulate activities the differentiation of the bone.

For example, the remodeling cycle involves bone resorption performed by osteoclasts. Osteoclasts remove the old or worn-out mineralized bone. Bone resorption is initiated when osteoclasts receive signals from the surface of bone that are stimulated by enzymes or cytokines. On the other hand, osteoblasts rebuild new bone tissue by laying down an unmineralized matrix, called osteoid, which will eventually form new mineralized bone.

When this rebuilding is complete, the area of bone remodeling rests until the next remodeling cycle begins. Under normal condition, bone resorption and formation are performed at the same time, thus the bone can renew without affecting bone's function.

As we march into the elder-populated society, osteoporosis that happens at youth is drawing more and more attention. Osteoporosis is not a disease of change in the bone component, but a decrease of bone mass. The decrease of bone density and bone strength make one more susceptible to accident and the resulting fracture or bone damages. The primary cause of osteoporosis is the imbalance of bone remodeling, the overly increase of osteoclasts and bone resorption. In addition, many female patients at menopause suffered from osteoporosis, suggesting that the lower of sex hormone (i.e. estrogen) is one of the causes of osteoporosis.

There are currently many agents available for osteoporosis on the market. For example, estrogen can treat osteoporosis. Therefore, steroid enzymes and derivatives similar to chemical structure of estrogen are regarded as potential agents for treating osteoporosis. In theory, the enzymes are not only applied to treat osteoporosis, but decrease the side effects caused by estrogen. However, the substantive examination has not studied yet.

In addition, JP H04-352795 disclosed agents that are hydroxyl containing steroidal hormones, having bone resorption antagonist or bone formation stimulatory activity. The agent acts as bone resorption antagonist. However, the actual experimental data have not been disclosed. JP H07-215878 disclosed an agent containing mepitiostane and epitiostanol as active ingredients for treating osteoporosis.

JP H08-12580 is related to a synostosis promotor containing a specific active vitamin D and its derivative as active ingredients, promoting bone-repairing step after extension of bone, cut of bone, fracture, etc., and useful for shortage of treating period and prevention and treatment for re-fracture.

JP H11-60489 disclosed a medicine for preventing/treating osteoporosis which enhances density and strength of bone without elevating the concentration of calcium in blood, by including an active type vitamin D and bisphosphonic acid as active ingredients.

However, the prior art above provides chemical compounds only, therefore cannot sufficiently treat osteoporosis.

BRIEF DESCRIPTION OF THE INVENTION

The present invention provides a composition for treating osteoporosis comprising *C. Sinensis* or the processed product of *C. Sinensis* as the effective ingredient.

The present invention further provides a composition for suppressing the formation of osteoclasts comprising *C. Sinensis* or the processed product of *C. Sinensis* as the effective ingredient.

DETAILED DESCRIPTION OF THE INVENTION

Figure 1:
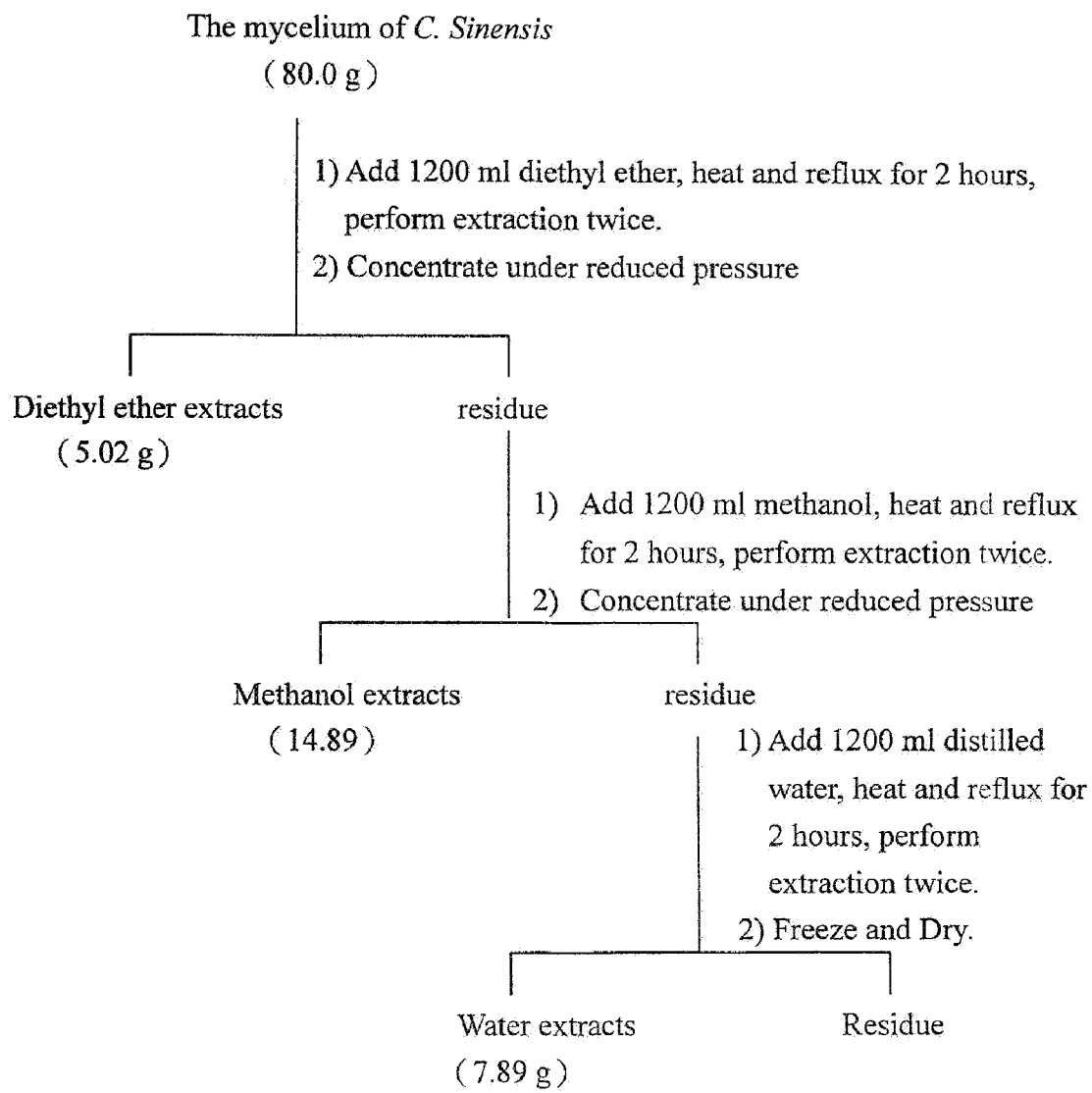
FIG. 1 discloses the procedure of preparing water extracts of the mycelium of *C. Sinensis*.

After extensive researches, the inventor has found *C. sinensis* to be effective in preventing osteoporosis. *C. Sinensis*, a plant of the ergot family, is a traditional and precious dried Chinese medicinal herb belonging to the fungus category. There are more than 300 species in the world, and the host in which *C. Sinensis* resides varies from insects to fungus. Depending on different hosts, the type of *C. Sinensis* parasites can be different. Sometimes different species of *C. Sinensis* resides on specifically the lava or the adult of the same insect.

As described above, many kinds of *C. Sinensis* are known to supplement health, provide energy and cure anemia. Recent researches have also shown that *C. Sinensis* has anti-tuberculosis bacterium activity and can expand bronchi as well as increase adrenaline secretion when administered.

The inventor has discovered another therapeutic effect of *C. Sinensis*. By administering certain amount of agent comprising the mycelium of *C. Sinensis* cultured and fermented by the specific process of the invention, the formation of osteoclasts was suppressed. In addition, the decrease of osteoclast formation is expected to rebalance bone resorption and bone formation, thereby preventing the decrease of bone density and improving osteoporosis.

Therefore, the invention provides a composition for treating osteoporosis comprising C. Sinensis or the processed product of C. Sinensis as the effective ingredient. The treatment of osteoporosis is made by suppressing the decrease of spongy bone density.

The invention further provides a composition for preventing the formation of osteoclasts comprising C. Sinensis or the processed product of C. Sinensis as the effective ingredient.

The invention further provides a composition for suppressing the decrease of spongy bone density comprising Cordyceps Sinensis or the processed product of Cordyceps Sinensis as the effective ingredient.

The preferred embodiment of C. Sinensis is the mycelium of C. Sinensis. The preferred embodiment of the processed product of C. Sinensis is prepared from water or organic solvent extract of mycelium of C. Sinensis. The organic solvent includes but is not limited to alcohol (such as $CH_3OH$, $C_2H_5OH$, $C_3H_7OH$), ester (such as acetyl acetate), alkane (such as hexane) and halogenated alkane (such as $CH_3C_1$, $C_2H_2Cl_2$). The preferred organic solvent is methanol, ethanol or alcoholic solvent without causing any side effect of human.

The invention further provides the method of preparing the processed product of the mycelium of C. Sinensis. The method comprises culturing the mycelium of C. Sinensis on slant culture or plate culture system. The preferred embodiment of the culture is the slant culture. The method further comprises procedures of 1. Potato cubes, glucose and agar were added into distilled water to prepare Potato Dextrose Agar (PDA)
2. Culture
   a. Slant culture
   PDA was dissolved in hot water until completely dissolved. 8 ml culture medium was added into 16×160 mm test tube. Then, the mixture was sterilized. Germ was cut with sterilized blazer and inoculated into slant medium. The medium was cultivated at 28° C.
   b. Plate culture
   PDA was added in water and divided into 5 sterilized culture flasks. After about 20 ml the culture medium was added to the plate. Germ was cut out with sterilized blazer and inoculated into slant medium. The medium was cultivated at 28° C.
   The mycelium of C. Sinensis from the medium was processed at cold temperature. The mycelium was separated from the medium. The separated mycelium was dried and smashed to obtain the powder of the mycelium of C. Sinensis.

The invention further provides the method of mass fermenting the processed product of the mycelium of C. Sinensis. The method comprises 1. Colonies were selected and grown in flasks.
2. After fermented in flask 1 and flask 2, large-scale fermentation was performed in production tank. The conditions of the production task were as follows: 96~136 hours, pH 5.5~6.0, air flow 0.2~0.3 vvm, 25~28° C.
3. The two stage mass production was fermented at 150~180 rpm, 25~28° C., for 8~10 days at pH 5.5~6.0.
4. The mycelium was separated from the culture medium. The dried mycelium was smashed, filled, sealed, packed and stored.

The most preferred embodiment of the processed product of C. Sinensis is the water extraction of C. Sinensis. The preferred concentration of the water extract is above 30 µg/ml. It has been found that the suppression of osteoclasts is less effective if the concentration is lower than 30 µg/ml. The better concentration is 30-3000 µg/ml. The most preferred concentration of the water extraction of the mycelium of C. Sinensis is 300~3000 µg/ml.

In addition, the composition of the invention further comprises non-toxic non active carriers in adjusted proportion to be administered to animals including human. The carriers can be in solid, semi-solid or liquid phase. The carrier can be selected from more than one dilute, filler or adjuvant.

The invention can be administered via intravenous, oral, intra-tissue, eye, nose, or colon route. The preferred embodiment is administration via oral route.

Oral administration can be administered in solid or liquid form, including in the form of powder, tablet, capsule, granule, droplet, solution, syrup, sublingual tablets or in other forms. The preferred embodiment is in the form of powder.

The preferred amount of the composition of the invention administered depends on the patient's condition and the administration route.

The preferred amount of the composition of the invention administrated to a normal adult is 25~250 mg/kg per day. The more preferred amount is 125~250 mg/kg per day. The administration may be divided into twice or four times a day.

EXAMPLES

First, the process of preparing the composition of the invention is described. The following examples demonstrate that the mycelium of C. Sinensis suppresses the formation of osteoclasts in vitro. The next example demonstrates the change of bone density (measured by DEXA (Dual energy X-ray absorptiometry) and pQCT (peripheral quantitative computed tomography)) after treating with the composition of the invention.

Example 1

The preparation of the Mycelium of C. Sinensis

The mycelium of C. Sinensis in this example could be cultured on slant culture or plate culture system.

1. 300.0 g potato cubes, 20.0 g glucose and 15.0 g agar were added into 1.0 L distilled water to prepare Potato Dextrose Agar (PDA)
2. Slant culture
   39 g PDA was dissolved in hot water (1.0 L) until completely dissolved. 8 ml culture medium was added into 16×160 mm test tube. Then, the mixture was sterilized at 121° C. for 20 min. $0.5^2$ mm of germ was cut with sterilized blazer and inoculated into slant medium. The medium was cultivated at 28° C.
3. Plate culture
   39 g PDA was added in 1 L water and separated into 5 culture flasks. The flasks were sterilized at 121° C. for 20 min. After about 20 ml the culture medium was added to the plate. $0.5^2$ mm of germ was cut out with sterilized blazer and inoculated into slant medium. The medium was cultivated at 28° C.
   The mycelium of C. Sinensis from the medium was processed at cold temperature. The mycelium was separated from the medium. The separated mycelium was dried and smashed to obtain the powder of the mycelium of C. Sinensis.
4. Mass fermentation
   Colonies were selected and were grown in flasks. After fermented in flask 1 and flask 2, large-scale fermentation was performed in production tank. The mycelium was separated from the culture medium. The dried mycelium was smashed, filled, sealed, packed and stored. The conditions of the production task were as follows: 96~136 hours, pH 5.5~6.0, air flow 0.2~0.3 vvm, 25~28° C. The two stage mass production was fermented at 150~180 rpm, 25~28° C., for 8~10 days at pH 5.5~6.0. In addition, water, starch, glucose and extractions of animal or plant proteins could be used in the culture medium.

Example 2

Water Extraction of C. sinensis Could Suppress the Development of Osteoclasts

Myelocytes and osteoblasts were co-cultured in vitro and the numbers of osteoclasts formed were measured. Myelocytes will differentiate into osteoclasts expressing tartrate-resisted acidic phosphatase (TRAP) when vitamin D is present in the coculture. These osteoclasts could be identified by staining for TRAP. Therefore the development of osteoclasts could be assayed by co-culturing myelocytes with osteoblasts.

Example 3

Preparation of Water Extraction of the Mycelium of C. sinensis

FIG. 1 showed the procedure of preparing the water extraction. First, 80 g of the mycelium of C. Sinensis was extracted by 1200 ml of diethyl ether until reflux. The extraction was repeated two times. Next, residue was extracted by 1200 ml of methanol until reflux. Likewise, the methanol extraction was formulated. Residue was extracted by 1200 ml of distilled water until reflux. Likewise, the water extraction was formulated.

Example 4

Co-Culture Procedure

Osteoblasts and, myelocytes were co-cultured in 24-well plate. PTH (100 ng/ml), $1\alpha, 25(OH)_2VD_3$ ($10^{-8}$ M), water extraction of the mycelium of C. Sinensis 3 mg/ml, 300 μg/ml, 30 μg/ml, 3 μg/ml or Elcatonin 2 U/ml were added. Samples were numbered No. 1~No. 6. Each sample was cultured in 4 wells. Culture was maintained for 6 days with medium changed every two days.

Example 5

Identification of Osteoclasts Formation

After coculturing, TRAP-positive cells were stained to dark red color. The numbers of TRAP-positive osteoclasts that have more than 3 nucleuses were counted. The average numbers of osteoclasts from 4 samples were the number of osteoclasts.

The numbers of osteoclasts in the $1\alpha, 25(OH)_2D_3$ sample was considered 100%. The percentage of osteoclasts formed of experimental group was calculated using formula 1. The result was shown in Table 1. Student's t-test was used to examine the significance.

The formation of osteoclasts (%) osteoclast cell numbers/ osteoclast cell numbers in medium with $1\alpha,25(OH)_2D_3 \times 100$ (formula 1)

TABLE 1

| Group | No. | Treatment | Average Osteoclast cell numbers (n = 4) | Formation of osteoclasts (%) | T-test | SD[#] |
|---|---|---|---|---|---|---|
| Exp. | 1 | The mycelium of C. Sinensis 3 mg/ml | 0.0 | 0.0 | 0.00 | 0.0 |
|  | 2 | The mycelium of C. Sinensis 300 μg/ml | 509.0 | 62.1 | 0.00 | 30.9 |
|  | 3 | The mycelium of C. Sinensis 30 μg/ml | 478.5 | 58.4 | 0.00 | 108.9 |
|  | 4 | The mycelium of C. Sinensis 3 μg/ml | 792.8 | 96.8 | 0.59 | 37.3 |
| Control | 5 | $1\alpha,25(OH)_2D_3$ $10^{-8}$ M | 819.0 | 100.0 |  | 69.4 |
|  | 6 | Elcatonin 2 U/ml | 113.0 | 13.8 | 0.00 | 15.7 |

[#]SD: Standard deviation.

As shown in Table 1, the formation of osteoclasts in the positive control—medium added with Elcatonin—was significantly different from the negative control ($1\alpha, 25(OH)_2 D_3$). The formation of osteoclasts in medium added with 30 μg/ml, 300 μg/ml and 3 mg/ml water extraction of C. Sinensis mycelium were 58.4% 62.1% and 0.0%, respectively. Thus, it is clear that water extractions of the mycelium of C. Sinensis can significantly suppress the formation of osteoclasts. The effect of adding 3 mg/ml water extraction of the mycelium of C. Sinensis (00) was even better than Elcatonin (13.8%). According to the in vitro tests, it suggest that water extraction of the mycelium of C. Sinensis mycelium suppressed the formation of osteoclasts against osteoporosis.

Example 6

Use Dual Energy X-Ray Absorptiometry (DEXA) to Measure the Effect of the Water Extraction of the Mycelium of C. Sinensis In Vivo Rats with ovaries removed were used as the model of osteoporosis. There were three groups to be tested. One control group was rats with sham operations, two other groups were rats with ovaries removed. One of the ovaries-removed groups was treated with water extraction of C. Sinensis. Whether the treatment can effectively lower one of the symptoms of osteoporosis—to decrease bone density, was evaluated by measuring the total bone density of lumbar. The total bone density was measured by the standard clinical technique DEXA.

The experiment procedures were as follows:
1. Eight month old rats were divided into 3 groups: ovary-removed (OVX) group, Sham group and ovary-removed group treated with water extractions of the mycelium of *C. Sinensis*. Each group included 7 rats.
2. First rats were anesthetized by intraperitonealy injecting amobarbital. Ovaries of rats in the OVX group were removed. Rats in the Sham group were also anesthetized, but their ovaries were not removed, only touched by tweezers.
3. 10 mg/kg, 50 mg/kg and 100 mg/kg water extractions of the mycelium of *C. Sinensis* were orally administered to rats. Administration was performed every 2 days for 5 weeks.
4. After 5 weeks, rats were anesthetized again using amobarbital. BMD (bone mass density) was measured by DEXA.

Anesthetized rats were put on sterilized table. DEXA was turned to small animal program (line specing and point resolution: 0.5×0.5 mm, scan speed: 15 mm/sec) to scan lumber spines. The average bone density of lumbar spine 2 to 4 (L2-L4) was measured. The significance was evaluated by Student's t-test.
5. Rats were put to euthanasia and ovaries were removed to measure ovary weight.

Figure 2:
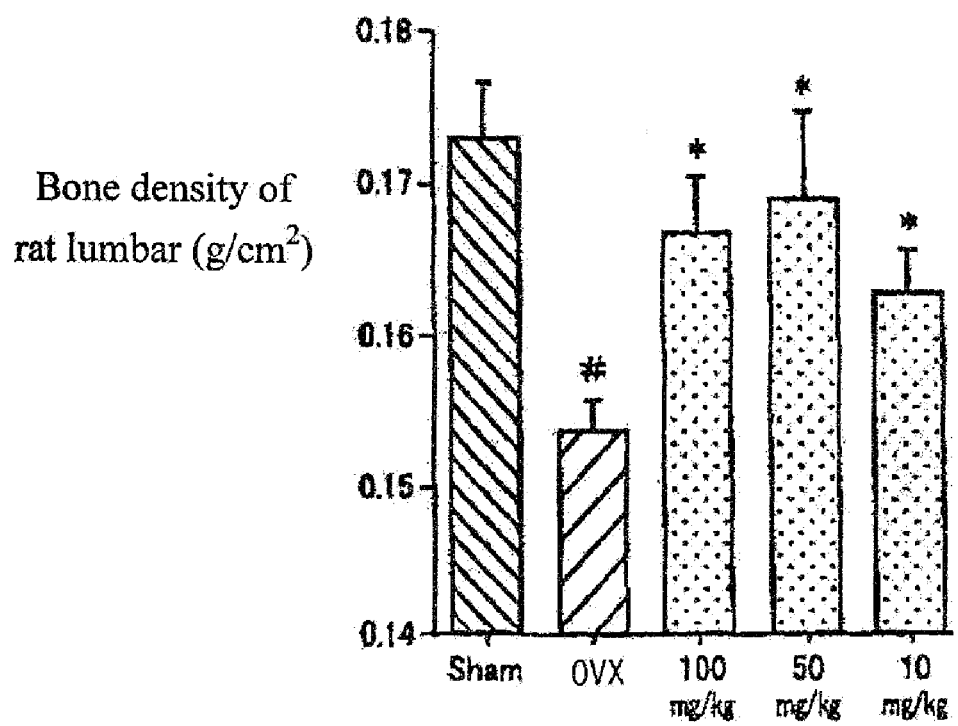
FIG. 2 discloses bone density of lumbar of rats from Sham (sham operation) group, OVX (ovary-removed control) group and ovary-removed rats treated with water extracts of the mycelium of *C. Sinensis* 10, 50, 100 mg/kg.

The results are shown in FIG. 2 and Table 2.

TABLE 2

|  | Sham | OVX | Water extraction of *C. Sinensis* mycelium (mg/kg) | | |
|---|---|---|---|---|---|
|  |  |  | 100 | 50 | 10 |
| Initial weight | 296 ± 4 | 298 ± 5 | 298 ± 3 | 298 ± 5 | 293 ± 6 |
| Final weight | 302 ± 4 | 334 ± 6 | 340 ± 7 | 331 ± 10 | 329 ± 6 |
| Ovary weight (mg)/100 gb.w. | 306 ± 53 | 46 ± 3 | 51 ± 3 | 49 ± 3 | 48 ± 3 |

$p < 0.01$ (compared to Sham)

As shown in FIG. 2 and Table 2, the body weights of rats in the OVX and Sham group were significantly different as expected, so were their ovary weights.

As shown in FIG. 2, there was a significant difference between OVX group and the group treated with the mycelium of *C. Sinensis*. Although the slowing of the decrease of BMD was not correlated with the concentration of the water extracts, the body and ovary weight was not affected. The inhibition of decreasing bone density of lumbar spine was lacking. Given the above, in vivo test about anti-osteoporosis activity was studied.

Example 7

Compare Bone Density by Peripheral Quantitative Computed Tomography (pQCT)

Similar to the DEXA experiment described above, rats with ovaries removed were administered with different concentrations of test substance.

In order to assess the manifestation of osteoporosis, the rat tibia was categorized into cortical bone and spongy bone. The density of cortical bone and spongy bone were measured and compared. Other SSI indexes of bone dymatics such as the length and bone strength of periosteum and endosteum were also compared. Bone density was measured by performing pQCT. The experiment procedure is described below.
1. 6-month-old female Wistar rats were grown for a week to familiarize to the environment.
2. After one week, rats were divided into ovaries-removed group, Sham group and ovaries-removed group. Each group included 7 rats.
3. One week after the operation, suspension of the mycelium of *C. Sinensis* 100 mg/kg was orally administrated, 3 times a week.
4. One month after the surgery, rats were anesthetized with 50 mg/kg amobarbital and bone dynamic data was measured by PQCT.
5. After completing the measure, rats were weighted and put to euthanasia using amobarbital and blood was collected. Serum was collected by centrifugation and was stored at −80° C.
6. Ovaries were removed and weighted.
7. Data was analyzed and statistically processed.

The result was shown in Table 3~Table 8. Table 3 showed the body and ovary weight. Table 4 showed the total bone mass, total bone density and section area. Table 5 was the total bone mass and density of spongy bone. Table 6 was the length of periosteum and endosteum. Table 7 was the bone mass, bone density and thickness of cortical bone of tibia. Table 8 showed the index of bone strength.

TABLE 3

| Group | Body weight (g) | Ovary weight (g) |
|---|---|---|
| Control | 326.8 ± 17.5 | 0.16 ± 0.03 |
| Sham | 307.5 ± 25.0 | 0.48 ± 0.06 |
| T-100 | 305.0 ± 12.6 | 0.15 ± 0.03 |

T-100 is suspension of the mycelium of *C. Sinensis* 100 mg/kg (1% CMC).

TABLE 4

| Group | n | Total bone mass | Total bone density | Tangential area |
|---|---|---|---|---|
| Control | 8 | 8.63 ± 0.60# | 672.65 ± 13.81# | 13.70 ± 1.22 |
| Sham | 4 | 9.93 ± 1.06 | 753.22 ± 32.26 | 13.16 ± 0.91 |
| T-100 | 7 | 8.36 ± 0.61 | 681.04 ± 47.08 | 12.30 ± 1.21 |

$p < 0.01$ (Compared to Sham)

As shown in Table 3, the body and uterus weights of mice in the ovary-removed group (control) and the Sham groups were significantly different, thus the ovary-removed mice were appropriate model organisms for osteoporosis. In addition, as shown in Table 4, the total bone mass and total bone density of tibia was not significantly different between mice of control group and the T-100 group. The total bone density, however, seemed to have increased.

TABLE 5

| Group | Spongy bone mass (mg/mm) | Spongy bone density (mg/cm$^3$) |
|---|---|---|
| Control | 0.85 ± 0.16 | 170.5 ± 27.8## |
| Sham | 0.84 ± 0.15 | 244.5 ± 40.0 |
| T-100 | 0.98 ± 0.21 | 210.3 ± 23.6* |

$p < 0.01$ (Compared to Sham)
*$p < 0.05$ (Compared to control)

As shown in Table 5, the major symptom of osteoporosis—the density of spongy bone, was significantly lowered in the group administered with mycelium of *C. Sinensis*. Therefore the powder of *C. Sinensis* mycelium is able to inhibit osteoporosis.

TABLE 6

| Group | periosteum length | endosteum length |
|---|---|---|
| Control | 12.53 ± 0.51 | 9.28 ± 0.54 |
| Sham | 12.85 ± 0.45 | 9.17 ± 0.24 |
| T-100 | 12.42 ± 0.63 | 9.25 ± 0.65 |

TABLE 7

| Group | Cortical bone mass | Cortical bone density | cortical bone |
|---|---|---|---|
| Control | 6.62 ± 0.37# | 1173.87 ± 18.27 | 0.52 ± 0.02# |
| Sham | 7.50 ± 0.67 | 1161.16 ± 18.20 | 0.59 ± 0.04 |
| T-100 | 6.27 ± 0.40 | 1146.62 ± 23.90 | 0.50 ± 0.01 | p < 0.05 (Compared to Sham)

TABLE 8

| Group | XSSI | YSSI | PSSI |
|---|---|---|---|
| Control | 3.43 ± 0.76# | 4.51 ± 1.31 | 7.31 ± 2.03 |
| Sham | 5.61 ± 1.81 | 5.64 ± 1.01 | 9.75 ± 1.23 |
| T-100 | 2.83 ± 0.41 | 3.21 ± 1.74 | 5.35 ± 2.65 | p < 0.05 (Compared to Sham)

The length of periosteum and endosteum as shown in Table 6, the bone mass, density and thickness of cortical bone as shown in Table 7, and the index of bone strength as shown in Table 8 were not significantly different among control and T-100 groups.

According to the examples above, the mycelium of C. Sinensis could suppress the formation of osteoclasts in vitro, thereby might inhibit bone resorption (bone erosion) in vivo. In the QCT experiment, since the mycelium of C. Sinensis could slow down the decrease of spongy bone density, thus the mycelium of C. Sinensis was able to suppress osteoporosis. In addition, measuring DEXA, pQCT had found that the bone density was significantly different. Given from the in vitro and in vivo studies above, the mycelium of C. Sinensis could suppress osteoporosis.

The effect of the present invention.

As discussed above, drug containing the mycelium of C. Sinensis, especially cultured C. Sinensis, of the present invention, could inhibit the formation of osteoclasts, slowed the decrease of bone density and thus inhibited osteoporosis when administered.

The invention claimed is:

1. A method for treating osteoporosis comprising administering to a patient in need of treatment, an effective amount of a composition comprising a water extract of an organic solvent extract of culture of *Cordyceps sinensis* as an effective ingredient.

2. The method according to claim 1, wherein the treatment of osteoporosis is made by suppressing a decrease of spongy bone density.

3. The method according to claim 1, wherein the *Cordyceps sinensis* is mycelium of *Cordyceps sinensis*.

4. The method according to claim 1, wherein at least one organic solvent is diethyl ether.

5. The method according to claim 1, wherein at least one organic solvent is selected from the group consisting of alcohol, ester, alkane and halogenated alkane.

6. The method according to claim 5, wherein the alcohol is methanol or ethanol.

7. The method according to claim 1, wherein said administering comprises at least one administration route selected from the group consisting of intravenous, oral, intra-tissue, eye, nose, and colon.

8. The method according to claim 1, wherein said composition is in a form selected from the group consisting of powder, tablet, capsule, granule, droplet, solution, syrup, and sublingual tablets.

* * * * *